(12) United States Patent
Leach et al.

(10) Patent No.: US 9,757,721 B2
(45) Date of Patent: Sep. 12, 2017

(54) CELL WASHING PLUNGER USING CENTRIFUGAL FORCE

(71) Applicant: Biomet Biologics, LLC, Warsaw, IN (US)

(72) Inventors: Michael D. Leach, Warsaw, IN (US); Randel Dorian, San Diego, CA (US); Richard W. Storrs, Berkeley, CA (US); Scott R. King, New Orleans, LA (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 14/708,547

(22) Filed: May 11, 2015

(65) Prior Publication Data
US 2016/0332158 A1 Nov. 17, 2016

(51) Int. Cl.
*A61M 1/00* (2006.01)
*A61M 1/02* (2006.01)
*A61M 1/36* (2006.01)
*B01L 3/00* (2006.01)
*B04B 5/04* (2006.01)

(52) U.S. Cl.
CPC .......... *B01L 3/502* (2013.01); *A61M 1/0281* (2013.01); *A61M 1/3692* (2014.02); *A61M 1/3696* (2014.02); *B01L 3/567* (2013.01); *B04B 5/0442* (2013.01); *A61M 1/0001* (2013.01); *B01L 2300/0832* (2013.01); *B01L 2400/0409* (2013.01); *B01L 2400/0478* (2013.01)

(58) Field of Classification Search
CPC .............. A61M 1/0001; A61M 1/0281; A61M 1/3692; A61M 1/3696; B01L 3/502; B01L 3/567; B01L 2300/0832; B01L 2400/0409; B01L 2400/0478; B04B 5/0442
See application file for complete search history.

(56) References Cited

U.S. PATENT DOCUMENTS

| | | | |
|---|---|---|---|
| 3,141,846 A | 7/1964 | Laven, Jr. | |
| 3,409,165 A | 11/1968 | Creith | |
| 3,420,374 A | 1/1969 | Umeda | |
| 3,441,143 A | 4/1969 | Kudlaty | |

(Continued)

FOREIGN PATENT DOCUMENTS

| | | |
|---|---|---|
| AU | 696278 | 1/1999 |
| BR | 9103724 | 3/1993 |

(Continued)

OTHER PUBLICATIONS

The Written Opinion of the International Searching Authority for PCT/US2016/030880, Aug. 12, 2016.*

(Continued)

*Primary Examiner* — David A Reifsnyder
(74) *Attorney, Agent, or Firm* — Schwegman Lundberg & Woessner, P.A.

(57) ABSTRACT

A method for washing a suspension of cells including a suspension fluid and a plurality of cells is provided. The method includes using centripetal force to generate a layer of wash solution against a cylindrical wall and to generate a cell suspension layer adjacent to the layer of wash solution. The method also includes forcing the cells through the layer of wash solution to generate a layer of clean cells. Devices for performing the method are also provided.

20 Claims, 12 Drawing Sheets

(56) References Cited

U.S. PATENT DOCUMENTS

| | | |
|---|---|---|
| 3,453,364 A | 7/1969 | Flodin et al. |
| 3,469,369 A | 9/1969 | Helmke |
| 3,508,653 A | 4/1970 | Coleman |
| 3,593,915 A | 7/1971 | Steinacker |
| 3,647,070 A | 3/1972 | Adler |
| 3,779,383 A | 12/1973 | Ayres |
| 3,785,549 A | 1/1974 | Latham, Jr. |
| 3,814,248 A | 6/1974 | Lawhead |
| 3,850,369 A | 11/1974 | Bull et al. |
| 3,879,295 A | 4/1975 | Glover et al. |
| 3,894,952 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,941,699 A | 3/1976 | Ayres |
| 3,972,812 A | 8/1976 | Gresl, Jr. |
| 3,982,691 A | 9/1976 | Schlutz |
| 4,001,122 A | 1/1977 | Griffin |
| 4,046,699 A | 9/1977 | Zine, Jr. |
| 4,055,501 A | 10/1977 | Cornell |
| 4,059,108 A | 11/1977 | Latham, Jr. |
| 4,077,396 A | 3/1978 | Wardlaw et al. |
| 4,152,270 A | 5/1979 | Cornell |
| 4,159,896 A | 7/1979 | Levine et al. |
| 4,187,979 A | 2/1980 | Cullis et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies et al. |
| 4,377,572 A | 3/1983 | Schwarz et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi |
| 4,427,650 A | 1/1984 | Stroetmann et al. |
| 4,427,651 A | 1/1984 | Stroetmann et al. |
| 4,442,655 A | 4/1984 | Stroetmann |
| 4,446,021 A | 5/1984 | Aufderhaar et al. |
| 4,453,939 A | 6/1984 | Zimmerman et al. |
| 4,464,167 A | 8/1984 | Schoendorfer et al. |
| 4,537,767 A | 8/1985 | Rothman et al. |
| RE32,089 E | 3/1986 | Blatt et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,974 A | 7/1989 | Kelley et al. |
| 4,853,137 A | 8/1989 | Ersson |
| 4,859,333 A | 8/1989 | Panzani |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,928,603 A | 5/1990 | Rose et al. |
| 4,929,242 A | 5/1990 | Desecki et al. |
| 4,933,291 A | 6/1990 | Daiss et al. |
| 4,943,273 A | 7/1990 | Pages et al. |
| 4,946,601 A | 8/1990 | Fiehler |
| 4,950,220 A | 8/1990 | Wells et al. |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,030,215 A | 7/1991 | Morse et al. |
| 5,030,341 A | 7/1991 | McEwen et al. |
| 5,045,048 A | 9/1991 | Kaleskas et al. |
| 5,053,127 A | 10/1991 | Schoendorfer et al. |
| 5,071,570 A | 12/1991 | Shiraki et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,204,537 A | 4/1993 | Bennet et al. |
| 5,206,023 A | 4/1993 | Hunziker |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,234,608 A | 8/1993 | Duff |
| 5,236,604 A | 8/1993 | Fiehler |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,370,802 A | 12/1994 | Brown |
| 5,376,263 A | 12/1994 | Fischel |

(56) References Cited

U.S. PATENT DOCUMENTS

| | | |
|---|---|---|
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,480,378 A | 1/1996 | Weis-Fogh et al. |
| 5,484,383 A | 1/1996 | Fitch, Jr. et al. |
| 5,494,578 A | 2/1996 | Brown et al. |
| 5,494,592 A | 2/1996 | Latham, Jr. et al. |
| 5,505,685 A | 4/1996 | Antwiler |
| 5,510,102 A | 4/1996 | Cochrum |
| 5,533,518 A | 7/1996 | Vogler |
| 5,560,830 A | 10/1996 | Coleman et al. |
| 5,577,513 A | 11/1996 | Van Vlasselaer |
| 5,585,007 A | 12/1996 | Antanavich et al. |
| 5,589,462 A | 12/1996 | Patat et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,632,905 A | 5/1997 | Haynes |
| 5,641,622 A | 6/1997 | Lake et al. |
| 5,643,192 A | 7/1997 | Hirsh et al. |
| 5,643,193 A | 7/1997 | Papillon et al. |
| 5,674,173 A | 10/1997 | Hlavinka et al. |
| 5,733,545 A | 3/1998 | Hood, III |
| 5,736,033 A | 4/1998 | Coleman et al. |
| 5,762,798 A | 6/1998 | Wenthold et al. |
| 5,788,662 A | 8/1998 | Antanavich et al. |
| 5,795,489 A | 8/1998 | Holm et al. |
| 5,795,571 A | 8/1998 | Cederholm-Williams et al. |
| 5,853,600 A | 12/1998 | McNeal et al. |
| 5,860,937 A | 1/1999 | Cohen |
| 5,889,584 A | 3/1999 | Wardlaw |
| 5,918,622 A | 7/1999 | Perez et al. |
| 5,924,972 A | 7/1999 | Turvaville et al. |
| 5,934,803 A | 8/1999 | Hutter |
| 5,958,253 A | 9/1999 | Holm et al. |
| 5,980,757 A | 11/1999 | Brown et al. |
| 6,011,490 A | 1/2000 | Tonnesen et al. |
| 6,022,306 A | 2/2000 | Dumont et al. |
| 6,025,201 A | 2/2000 | Zelmanovic et al. |
| 6,027,655 A | 2/2000 | Holm |
| 6,051,146 A | 4/2000 | Green et al. |
| 6,053,856 A | 4/2000 | Hlavinka |
| 6,054,122 A | 4/2000 | MacPhee et al. |
| 6,063,297 A | 5/2000 | Antanavich et al. |
| 6,071,423 A | 6/2000 | Brown et al. |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,153,113 A | 11/2000 | Goodrich et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 | 4/2001 | Antanavich et al. |
| 6,245,900 B1 | 6/2001 | Yamasaki et al. |
| 6,274,090 B1 | 8/2001 | Coelho et al. |
| 6,277,961 B1 | 8/2001 | Hock et al. |
| 6,280,400 B1 | 8/2001 | Niermann |
| 6,296,602 B1 | 10/2001 | Headley |
| 6,316,247 B1 | 11/2001 | Katz et al. |
| 6,322,785 B1 | 11/2001 | Landesberg et al. |
| 6,334,842 B1 | 1/2002 | Hlavinka et al. |
| 6,342,157 B1 | 1/2002 | Hood, III |
| 6,368,298 B1 | 4/2002 | Beretta et al. |
| 6,464,624 B2 | 10/2002 | Pages |
| 6,472,162 B1 | 10/2002 | Coelho et al. |
| 6,516,953 B1 | 2/2003 | DiCesare et al. |
| 6,544,162 B1 | 4/2003 | Van Wie et al. |
| 6,563,953 B2 | 5/2003 | Lin et al. |
| 6,596,180 B2 | 7/2003 | Baugh et al. |
| 6,629,919 B2 | 10/2003 | Egozy et al. |
| 6,676,629 B2 | 1/2004 | Andrew et al. |
| 6,758,978 B1 | 7/2004 | Bedell |
| 6,764,531 B2 | 7/2004 | Hogan |
| 6,777,231 B1 | 8/2004 | Katz et al. |
| 6,830,762 B2 | 12/2004 | Baugh et al. |
| 6,905,612 B2 | 6/2005 | Dorian et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,179,391 B2 | 2/2007 | Leach et al. |
| 7,694,828 B2 | 4/2010 | Swift et al. |
| 7,708,152 B2 | 5/2010 | Dorian et al. |
| 7,824,559 B2 | 11/2010 | Dorian et al. |
| 7,901,584 B2 | 3/2011 | Dorian et al. |
| 7,987,995 B2 | 8/2011 | Dorian et al. |
| 8,096,422 B2 | 1/2012 | Dorian et al. |
| 8,105,495 B2 | 1/2012 | Dorian et al. |
| 8,133,389 B2 | 3/2012 | Dorian et al. |
| 2002/0032112 A1 | 3/2002 | Pages |
| 2002/0076400 A1 | 6/2002 | Katz et al. |
| 2003/0082152 A1 | 5/2003 | Hedrick et al. |
| 2003/0191429 A1 | 10/2003 | Andrew et al. |
| 2004/0171146 A1 | 9/2004 | Katz et al. |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0109716 A1 | 5/2005 | Leach et al. |
| 2005/0153441 A1 | 7/2005 | Hedrick et al. |
| 2005/0153442 A1 | 7/2005 | Katz et al. |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0083720 A1 | 4/2006 | Fraser et al. |
| 2006/0175242 A1 | 8/2006 | Dorian et al. |
| 2006/0175244 A1 | 8/2006 | Dorian et al. |
| 2006/0196885 A1 | 9/2006 | Leach et al. |
| 2006/0243676 A1 | 11/2006 | Swift et al. |
| 2007/0036768 A1 | 2/2007 | Fraser et al. |
| 2007/0075016 A1 | 4/2007 | Leach |
| 2008/0011684 A1 | 1/2008 | Dorian et al. |
| 2008/0283474 A1 | 11/2008 | Leach et al. |
| 2009/0289014 A1 | 11/2009 | Hoeppner |
| 2010/0206798 A1 | 8/2010 | Dorian et al. |
| 2010/0226909 A1 | 9/2010 | Hecker et al. |
| 2014/0047986 A1 | 2/2014 | Robinson |
| 2016/0288139 A1* | 10/2016 | Leach ............ A61M 1/0281 |

FOREIGN PATENT DOCUMENTS

| | | |
|---|---|---|
| CA | 1321138 | 8/1993 |
| CA | 2182862 | 6/1996 |
| CN | 1074709 | 7/1993 |
| DE | 56103 | 10/1860 |
| DE | 1443359 | 11/1968 |
| DE | 3321466 A1 | 12/1983 |
| DE | 4202667 | 5/1993 |
| EP | 090997 | 10/1983 |
| EP | 0097455 A2 | 1/1984 |
| EP | 0102773 | 3/1984 |
| EP | 0109374 | 5/1984 |
| EP | 0142339 | 5/1985 |
| EP | 0253198 | 1/1988 |
| EP | 0272915 A2 | 6/1988 |
| EP | 285891 | 10/1988 |
| EP | 0295771 | 12/1988 |
| EP | 0295771 A2 | 12/1988 |
| EP | 0417818 | 3/1991 |
| EP | 0534178 | 3/1993 |
| EP | 0592242 | 4/1994 |
| EP | 1005910 | 6/2000 |

(56) References Cited

FOREIGN PATENT DOCUMENTS

| | | |
|---|---|---|
| EP | 1427279 A1 | 6/2004 |
| EP | 1467746 A2 | 10/2004 |
| EP | 1670315 A2 | 6/2006 |
| EP | 1716901 | 11/2006 |
| GB | 854715 | 11/1960 |
| JP | 60-053845 | 3/1985 |
| JP | 60250014 A | 12/1985 |
| JP | 63182055 A | 7/1988 |
| JP | 6454256 | 4/1989 |
| JP | 2036872 | 2/1990 |
| JP | 02071747 | 3/1990 |
| JP | 04500170 T | 1/1992 |
| JP | 6250014 A | 9/1994 |
| JP | 09187504 A | 7/1997 |
| JP | 9509432 T | 9/1997 |
| JP | 11502502 T | 3/1999 |
| JP | 2000117150 A | 4/2000 |
| JP | 02129224 | 10/2000 |
| JP | 2001017540 A | 1/2001 |
| JP | 2005523128 T | 8/2005 |
| MX | 246078 | 5/2007 |
| WO | WO-8400905 | 3/1984 |
| WO | WO-8802259 | 4/1988 |
| WO | WO-8901827 A1 | 3/1989 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9616714 A1 | 6/1996 |
| WO | WO-9617871 A1 | 6/1996 |
| WO | WO-9848938 A1 | 11/1998 |
| WO | WO-0103756 | 1/2001 |
| WO | WO-0183068 | 11/2001 |
| WO | WO-0224107 | 3/2002 |
| WO | WO-03015800 | 2/2003 |
| WO | WO-03024215 A1 | 3/2003 |
| WO | WO-03/053362 A2 | 7/2003 |
| WO | WO-03/092894 | 11/2003 |
| WO | WO-03090839 A1 | 11/2003 |
| WO | WO-2004/009207 | 1/2004 |
| WO | WO-2004037427 A1 | 5/2004 |
| WO | WO-2004104553 | 12/2004 |
| WO | WO-2005034843 A2 | 4/2005 |
| WO | WO-2006081699 A1 | 8/2006 |
| WO | WO-2007142908 A1 | 12/2007 |
| WO | WO-2011008836 A1 | 1/2011 |
| WO | WO-2016160451 A1 | 10/2016 |
| WO | WO 2016182830 A1 * | 11/2016 |

OTHER PUBLICATIONS

"International Application No. PCT/US2016/030880, Invitation to Pay Additional Fees and Partial Search Report mailed Aug. 12, 2016", 6 pgs.

"U.S. Appl. No. 14/672,335, Response filed Feb. 15, 2017 to Restriction Requirement mailed Dec. 15, 2016", 8 pgs.

"U.S. Appl. No. 14/672,335, Restriction Requirement mailed Dec. 15, 2016", 6 pgs.

"International Application Serial No. PCT/US2016/023762, International Search Report mailed Jun. 16, 2016", 4 pgs.

"International Application Serial No. PCT/US2016/023762, Written Opinion mailed Jun. 16, 2016", 5 pgs.

"International Application Serial No. PCT/US2016/030880, International Search Report mailed Oct. 5, 2016", 7 pgs.

* cited by examiner

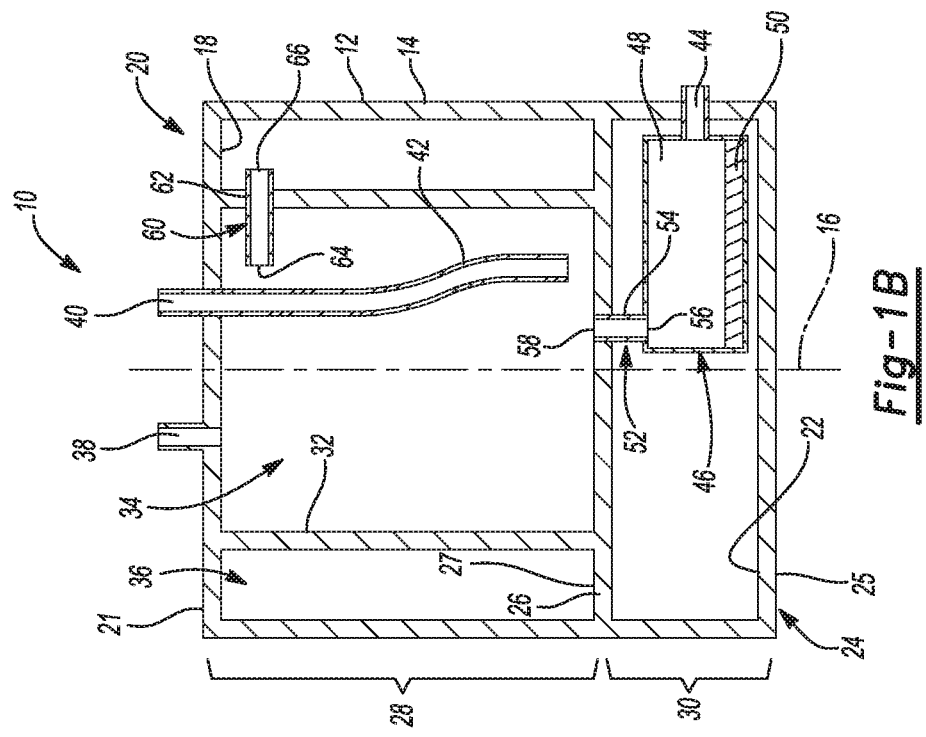
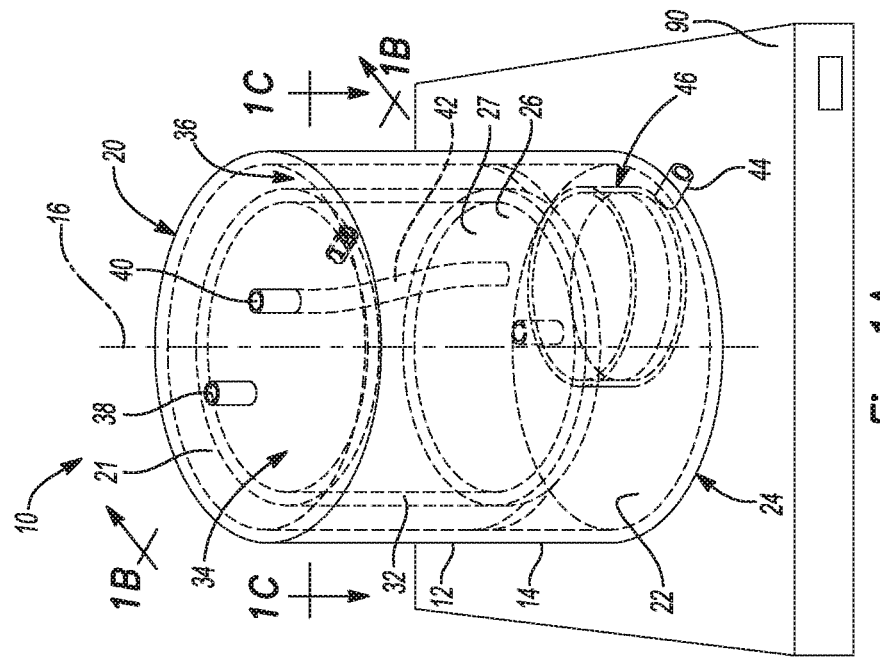

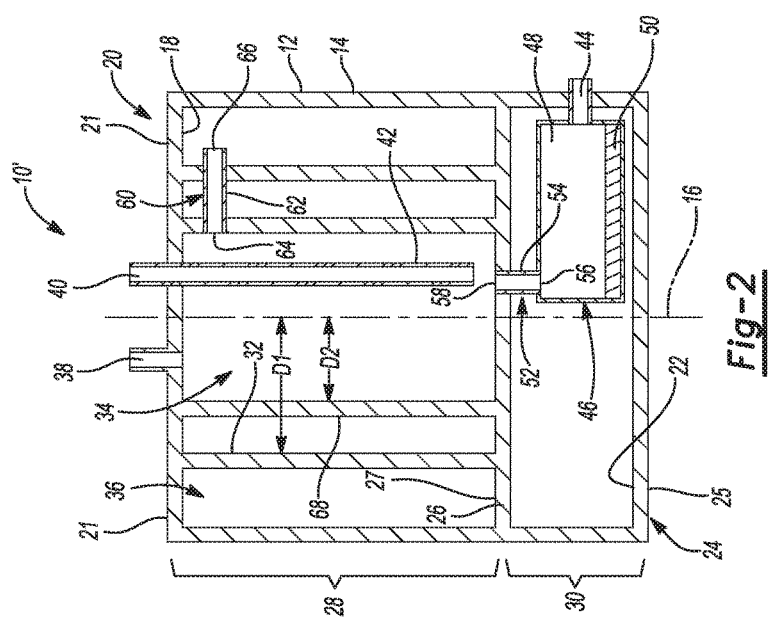
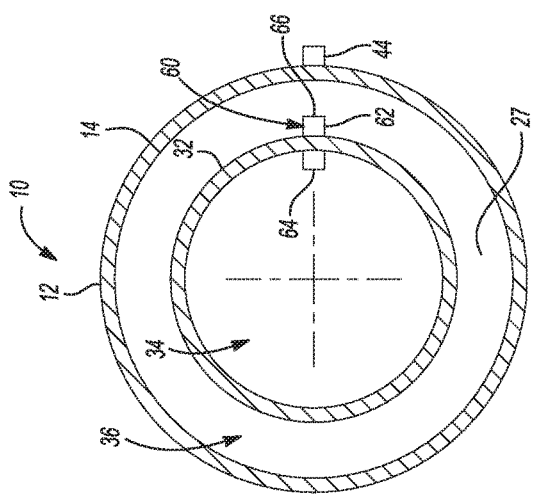

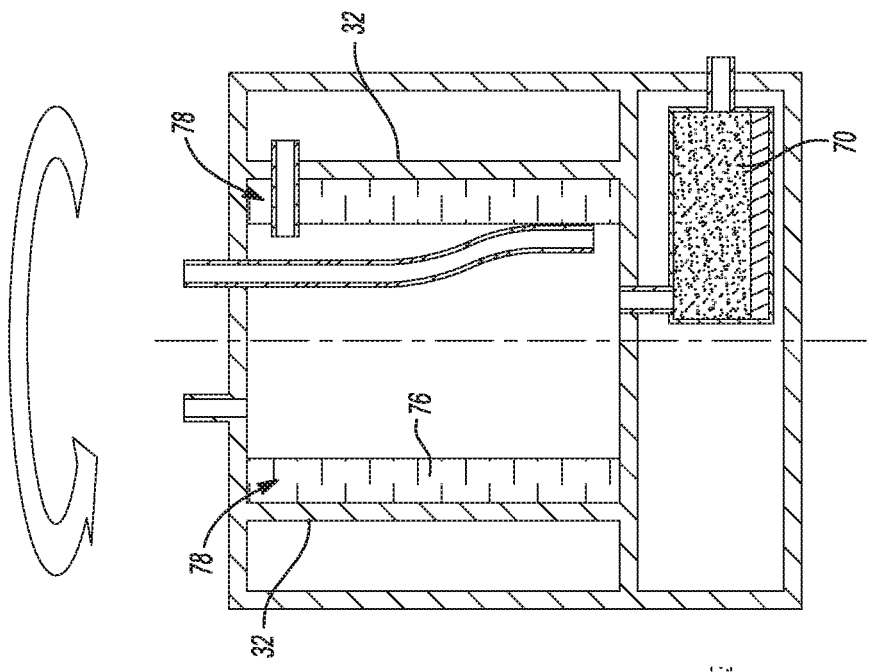
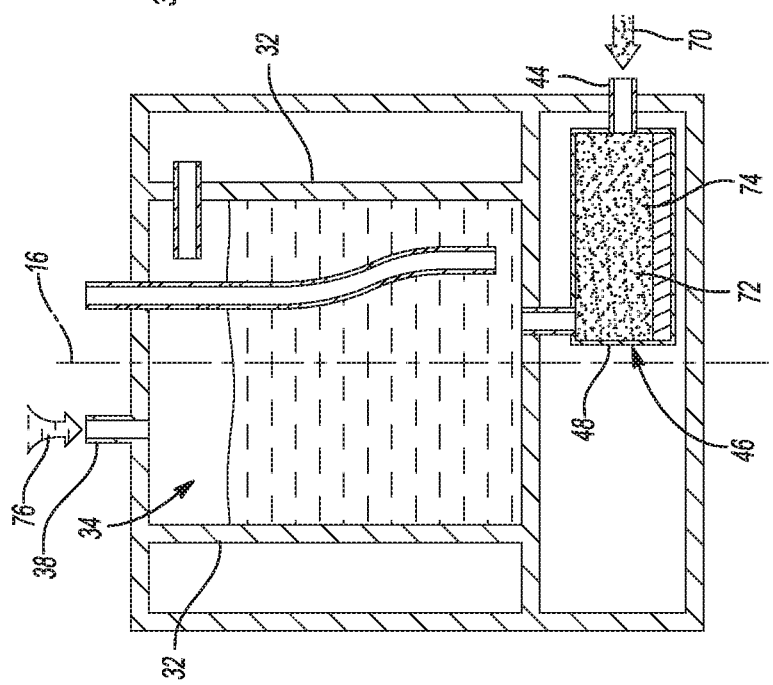

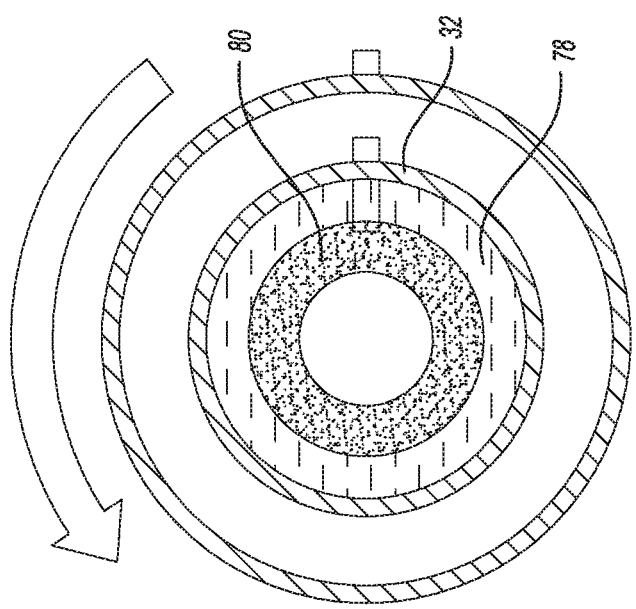
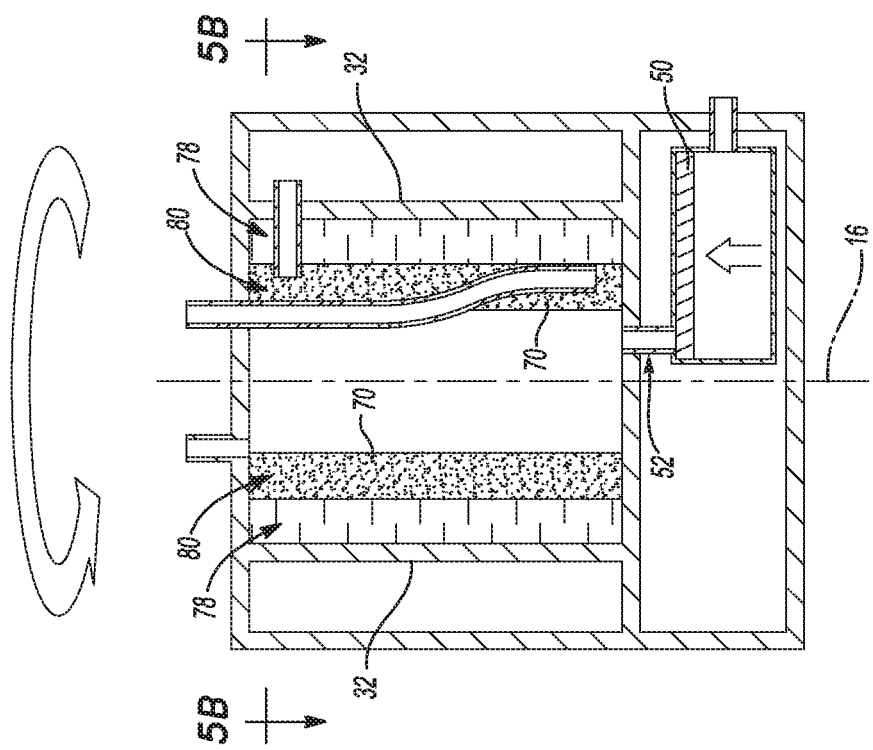
Fig-5B
Fig-5A

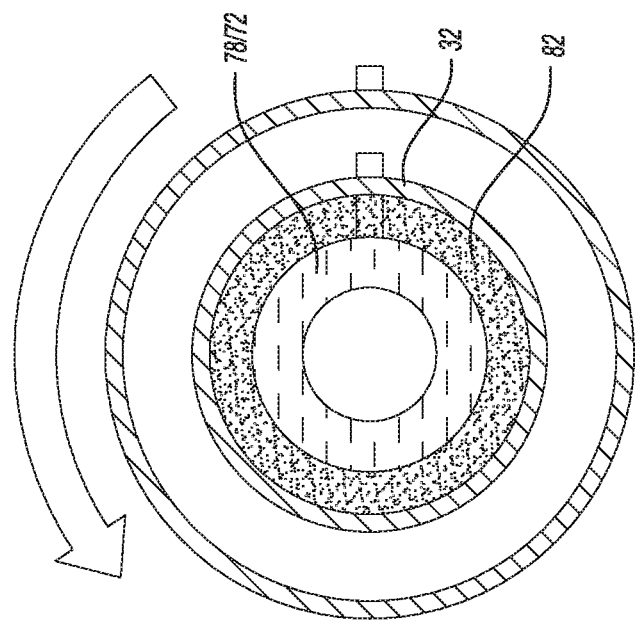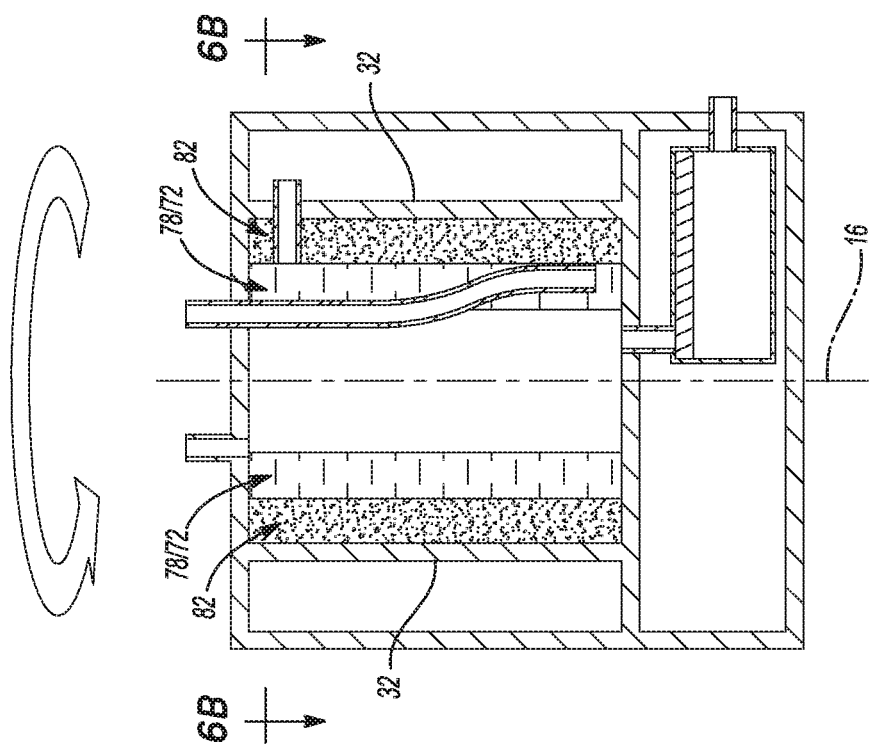

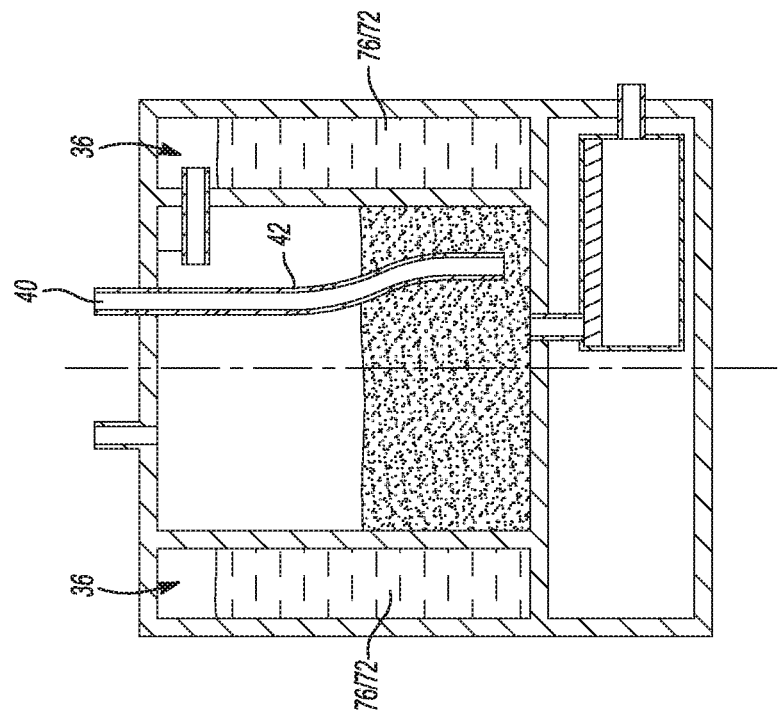
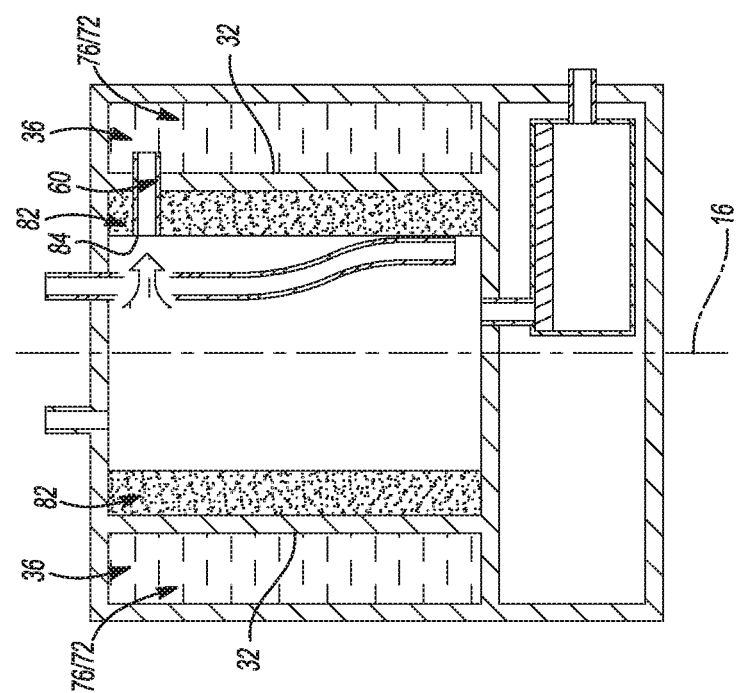

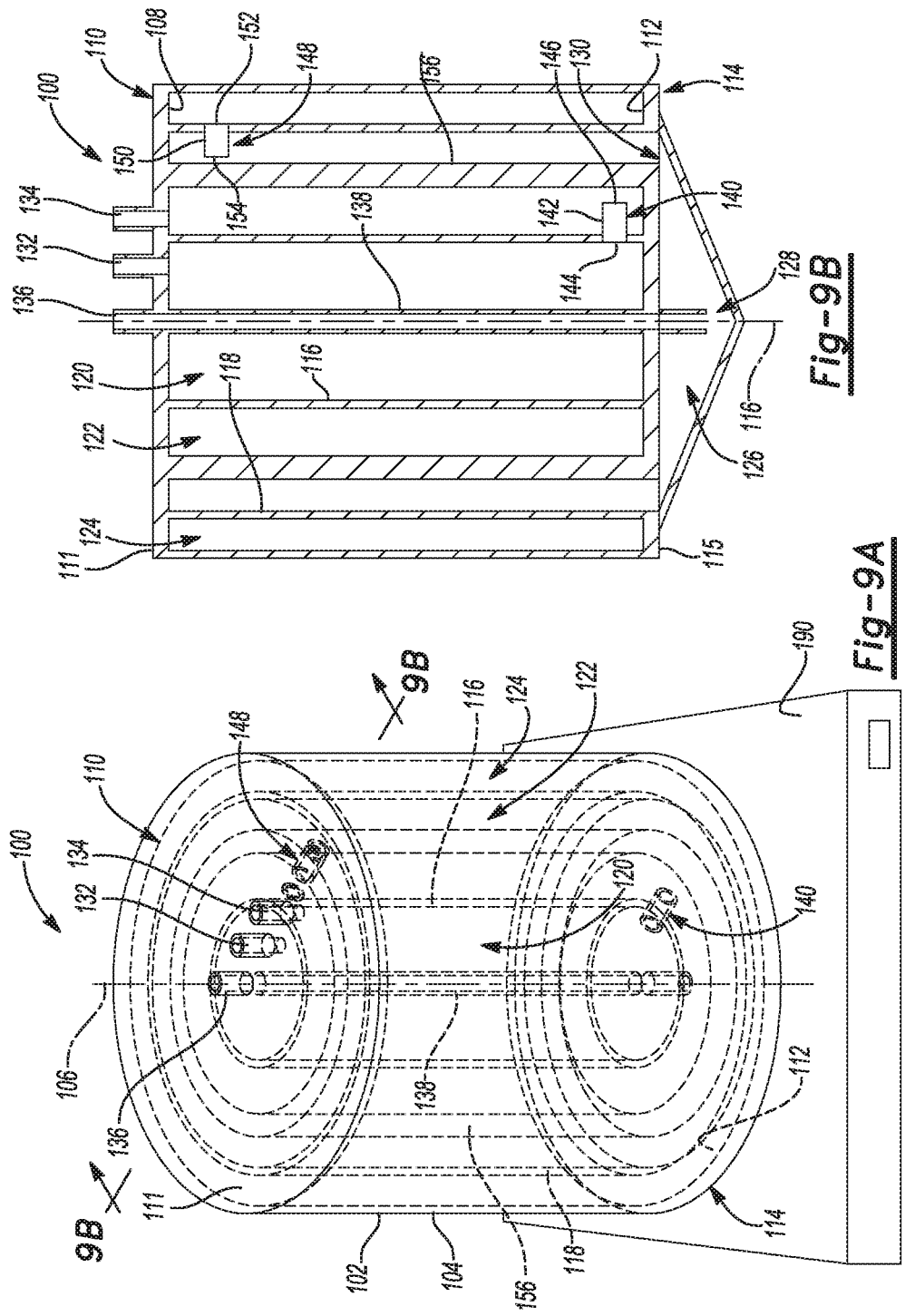

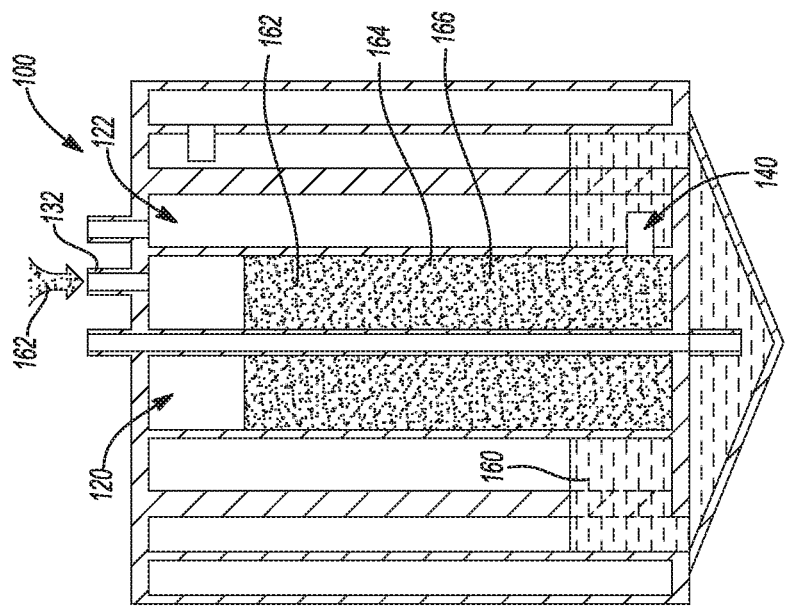
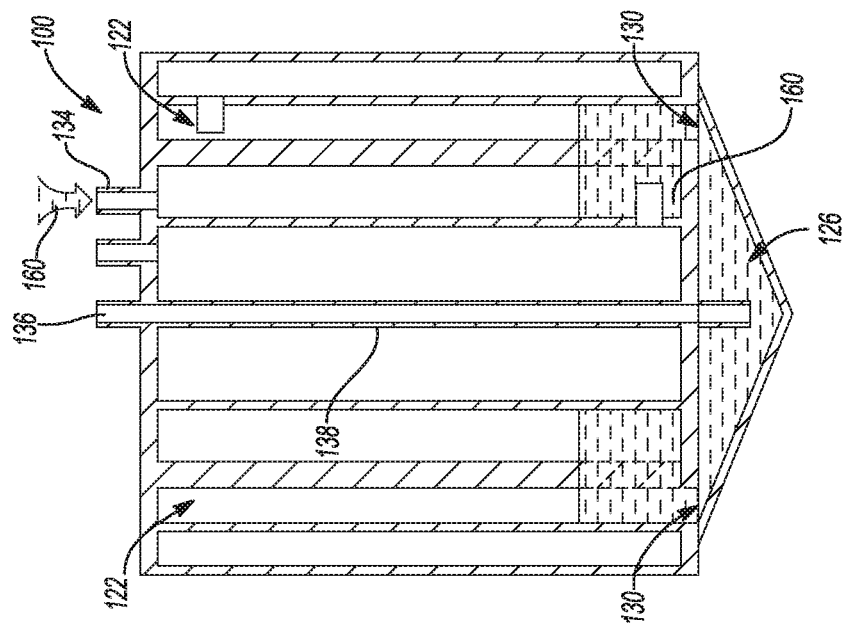

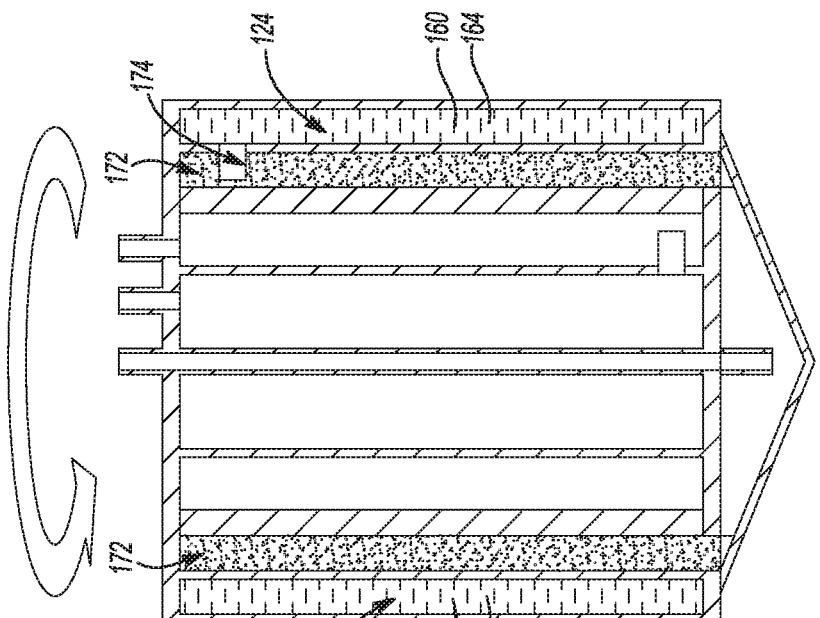
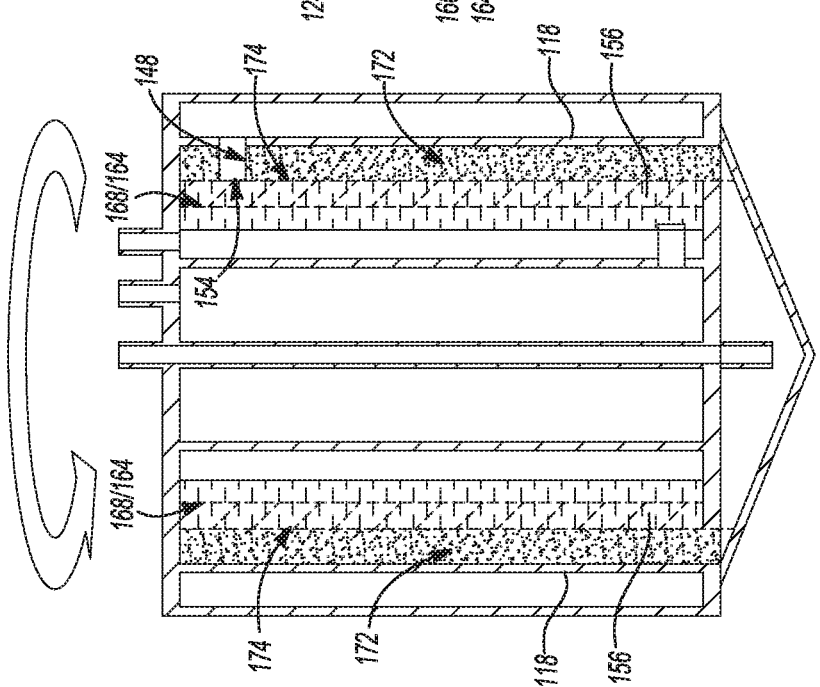

CELL WASHING PLUNGER USING CENTRIFUGAL FORCE

FIELD

The present disclosure relates to washing a suspension of cells, and particularly to washing cells with centrifugal force.

BACKGROUND

This section provides background information related to the present disclosure which is not necessarily prior art.

Blood transfusions are used to treat many disorders and injuries, such as in the treatment of accident victims and during surgical procedures. According to current American Red Cross statistics, about 5 million people receive blood transfusions each year, in the United States alone. Thus, health care systems rely on the collection and distribution of blood. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. When a subject is in need of a blood transfusion, a unit of blood is commonly removed from storage, rejuvenated, washed, and resuspended in an appropriate solution. In some instances, the red blood cells were lyophilized prior to storage, in which case they need to be resuspended, washed, and then resuspended again in an appropriate solution. The resuspended red blood cells are then transfused into the subject. In either scenario, washing the red blood cells is traditionally a tedious, time consuming and multistep process that requires a great deal of tubing, and the use of expensive centrifuges with rotating seals to separate the cells from the wash solution. Therefore, there remains a need to streamline and simplify the process for washing red blood cells prior to transfusion.

SUMMARY

This section provides a general summary of the disclosure, and is not a comprehensive disclosure of its full scope or all of its features.

The present technology provides a method for washing a suspension of cells, such as a plurality of cells in a suspension fluid. In one embodiment, the plurality of cells includes red blood cells and the suspension fluid includes an enhancement composition. The method includes introducing a wash solution into a compartment of a device having a cylindrical inner wall and rotating the device to a first centripetal force that causes the wash solution to form a layer of wash solution against the inner wall. The method also includes introducing a suspension of cells into the compartment. Rotating the device to a second centripetal force causes the suspension of cells to form a layer of suspended cells adjacent to the layer of washing solution. The method additionally includes rotating the device to a third centripetal force that causes the cells to pass through and displace the layer of wash solution to generate a layer of clean cells adjacent to the inner wall. The method also includes collecting the clean suspension of cells from the device.

A device for washing a suspension of cells is also provided. The device comprises a housing that defines a cylindrical out wall that extends about and along a central longitudinal axis from a first inner surface of a first end to a second inner surface of a second end. The device also has a first outer surface on the first end and a second outer surface at the second end. A first cylindrical inner wall extends about and along the axis from the first inner surface to the second inner surface to define a first compartment and a second compartment. The second compartment is adjacent to and concentric with the first compartment. Also, the device includes a first valve assembly including a first internal valve. The first valve assembly is positioned through the first inner wall such that the first compartment is in fluid communication with the second compartment when the valve is open. The device also has a first inlet port and an outlet port. Methods for using the device are also provided.

Also provided is another device for washing a suspension of cells. The device includes a housing that defines a cylindrical wall that extends about and along a central longitudinal axis from a first surface of a first end to a second surface of a second end. The device also includes a first planar separator and a second planar separator. The first and second planar separators are orthogonal to the axis and the wall. Additionally, the first and second planar separators define consecutive first, second, and third compartments from the first end to the second end. A first inlet is positioned on the first end and is in fluid communication with the first compartment. A second inlet is positioned on the first end and is in fluid communication with the second compartment by way of a conduit. Methods for using the device are also provided.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1A is a graphic illustration of a first device according to the present technology;

FIG. 1B is cross-sectional view of the device of FIG. 1A taken along line 1B;

FIG. 1C is a cross-section view of the device of FIG. 1A taken along line 1C;

FIG. 2 is a cross-sectional view of a device that is similar to the device shown in FIG. 1A, but having an optional porous screen;

FIGS. 3-8 are graphic illustrations of various stages of the device of FIG. 1A when being used to wash a suspension of cells, wherein FIG. 5B shows a cross-sectional view of FIG. 5A taken along line 5B and FIG. 6B shows a cross-sectional view of FIG. 6A taken along line 6B;

FIG. 9A is a graphic illustration of a second device according to the present technology;

FIG. 9B is a cross-sectional view of the device of FIG. 9A taken along line 9B;

FIGS. 10-16 are graphic illustrations of various stages of the device of FIG. 9A when being used to wash a suspension of cells;

Corresponding reference numerals indicate corresponding parts throughout the several views of the drawings.

DETAILED DESCRIPTION

Figure 12:
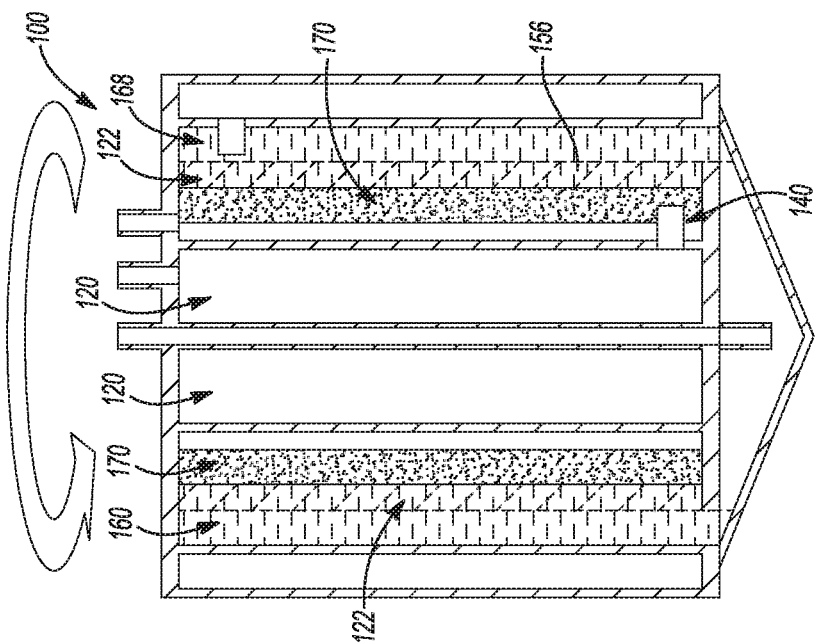

Example embodiments will now be described more fully with reference to the accompanying drawings.

The present technology generally provides devices and methods for washing a suspension of cells. The devices and methods rely on centripetal force to pass a suspension of cells through a wash solution. The cells are then isolated from the wash solution. Accordingly, the devices according to the present technology do not require much, if any, tubing. Rotating seals are not required in the device and the only movements necessary are spinning of a rotor and depression of a plunger or opening of at least one valve as described in detail below. The devices provide quick and easy methods for washing a suspension of cells, which, for example, can be administered to a human or other animal subject in need thereof.

The devices can be used to separate a component from a multicomponent mixture. For example, cells can be separated from a multicomponent mixture in order to separate the cells from an unwanted component, which results in washed cells. Different types of cells are often treated with various compositions, which results in a need to separate the cells from treatment solutions and particulate matter, such as cell fragments and cellular debris. According to the present technology, cells can be washed in any wash solution commonly known in the art. However, in various embodiments the wash solution is not less dense than the fluid in which the cells are suspended. In other embodiments, the wash solution is denser and/or has a higher specific gravity than the fluid in which the cells are suspended. Non-limiting examples of wash solutions include water, saline, dextrose, saline with 5% dextrose, dextran 40 (such as, for example, 10% dextran 40 in 0.9% sodium chloride or in 5% dextrose), hetastarch solutions (such as, for example, 6% hetastarch in 0.9% sodium chloride), phosphate buffered saline, and other solution that are used to remove unwanted components from cells. The cells may then be administered to a subject, such as a human or non-human mammal, or otherwise manipulated or stored. Non-limiting examples of cells that can be treated and washed include cells in whole blood, red blood cells, platelets, adipocytes, chondrocytes, and mixtures thereof. For example, because stored red blood cells (RBCs) have a diminished capacity to oxygenate tissues, a suspension of RBCs removed from storage can be rejuvenated by adding an enhancement composition, such as Rejuvesol® Red Blood Cell Processing Solution (Citra Labs, LLC, Braintree, Mass.), to the RBCs to form a multicomponent mixture or a suspension of cells. The suspension of cells including rejuvenated RBCs and a wash solution are then introduced into a device provided herein, wherein the RBCs are washed. During the wash, the RBCs are separated and isolated from the enhancement composition and optionally from unwanted cellular debris. The RBCs can then be used as concentrated RBCs or they can be resuspended in a reconstitution solution to achieve a desired RBC concentration.

The present technology provides a method for washing a suspension of cells. The suspension of cells includes a suspension fluid and a plurality of cells, such as red blood cells. The method comprises introducing a wash solution into a cylindrical compartment of a device having a cylindrical inner wall that extends about and along a longitudinal central axis from a first surface at a first end to a second surface at a second end. In some embodiments, the wash solution is selected from the group consisting of water, saline, dextrose, saline with 5% dextrose, dextran 40 (such as, for example, 10% dextran 40 in 0.9% sodium chloride or in 5% dextrose), hetastarch solutions (such as, for example, 6% hetastarch in 0.9% sodium chloride), and phosphate buffered saline. The method then comprises rotating the device about the center axis at a first speed to generate a first centripetal force. The first centripetal force causes the wash solution to push against the inner wall to form a layer of wash solution at the inner wall. Then, the method includes introducing the suspension of cells into the cylindrical compartment and rotating the device at a second speed to generate a second centripetal force. The second centripetal force is greater than the first centripetal force. The second centripetal force causes the suspension of red blood cells to push against the layer of wash solution to form a layer of suspended cells adjacent to the layer of wash solution. In various embodiments, the density and/or specific gravity of the wash solution is equal to or greater than the density and/or specific gravity of the suspension fluid, which facilitates formation of two distinct layers, i.e., the layer of wash solution and the layer of suspended cells, which are separated by an interface. The denser the wash solution is relative to the suspension fluid, the more defined the interface between the wash solution and suspension of cells will be. The method then comprises rotating the device at a third speed to generate a third centripetal force. The third centripetal force is greater than the second centripetal force and causes the cells in the layer of suspended cells to migrate through the interface, through the layer of wash solution, and to the inner wall. This migration results in separating the red blood cells from the suspension of red blood cells and the wash solution and displacing the layer of wash solution to form a layer of clean cells. The method also includes isolating the clean cells by removing the wash solution and suspension fluid from the compartment. Finally, the method includes removing the isolated clean cells from the device.

A device 10 according to the present technology, which can be used to perform the method for washing a suspension of cells, is shown in FIG. 1. FIGS. 1B and 1C show cross-sectional perspectives of the device 10 of FIG. 1A taken along lines 1B and 1C, respectively. The device 10 comprises a housing 12 that defines a cylindrical outer wall 14 that extends about and along a central longitudinal axis 16 from a first inner surface 18 at a first end 20 to a second inner surface 22 at a second end 24. The first end 20 includes a first outer surface 21 and the second end 24 includes a second outer surface 25. In various embodiments, the first and second inner and outer surfaces 18, 22, 21, 25 are planar. The device 10 also includes an inner plate 26 that has a third inner surface 27. The inner plate 26 is positioned between the first and second ends 20, 24. The inner plate 26 is planar and orthogonal to the axis 16, and bifurcates the device 10 into an inner washing region 28 and an inner loading region 30. Also, the device 10 includes a cylindrical inner wall 32 that extends about and along the axis 16 from the first inner surface 18 to the third inner surface 27 in the washing region 28 of the device 10. The first inner wall 32 defines a first center compartment 34 and a second compartment 36 in the washing region 28, wherein the second compartment 36 is adjacent to and concentric with, i.e., they share the same central axis 16, the center compartment 34.

The device 10 also comprises a first inlet port 38 and an outlet port 40. The first inlet port 38 is positioned at the first end 20 and is in fluid communication with the first compartment 34. The outlet port 40 is also positioned at the first end 20, but is in fluid communication with the first compartment 34. However, in various embodiments, the outlet port 40 is in fluid communication with the first compartment 34 by way of a conduit 42 that extends to or near the third inner surface 27, such that when gravity pulls a composition, solution, or collection of cells to the third inner surface 27, all or most of the composition, solution, or collection of cells can be removed from the device 10 through the outlet port 40.

Additionally, the device 10 comprises a second inlet port 44 for introducing a suspension of cells into the device 10 and a plunger assembly 46 that includes a barrel 48 and a plunger 50. In FIGS. 1A-1B, the second inlet port 44 is positioned at the outer wall 14 of the device 10. However, in other embodiments, the second inlet port 44 may be positioned on another surface, such as the second outer surface 25. The plunger assembly 46 is positioned in the loading region 30 of the device 10. Therefore, in any configuration, the inlet port 44 is in fluid communication with the barrel 48 of the plunger assembly, such that a suspension of cells can be loaded into the barrel 48 of the plunger assembly 46 by way of the second inlet port 44. However, once loaded, the contents of the barrel 48 cannot flow back and out of the device 10 through the second inlet port 44. For example, the second inlet port can be capped or plugged to prevent leaking after the barrel 48 is loaded. Although the first and second inlet ports 38, 44 and the outlet port 40 are shown protruding from the device 10, it is understood that all the ports 38, 40, 44 can be in line, i.e., flat, with their respective surfaces to preclude protrusions when the device 10 is in use.

In various embodiments, a first valve assembly 52 comprising a tubular body 54 that extends from a first end 56 to a second end 58 and a first internal valve (not shown) is positioned between the barrel 48 of the plunger assembly 46 and the first compartment 34, such that the barrel 48 is in fluid communication with the first compartment 34 when the valve is open. The valve of the first valve assembly 52 is normally in a closed position prior to use. During use, the valve is actuated to an open position mechanically, electrically, or magnetically, at a predetermined centripetal force or pressure. Non-limiting examples of valves that are actuated by centripetal force and that are suitable for the first valve assembly 52 are described in U.S. Pat. No. 7,824,559 issued to Dorian et al. on Aug. 10, 20016, and U.S. Pat. No. 7,708,152 issued to Dorian et al. on May 4, 2010, both of which are incorporated herein by reference. In some embodiments the valve of the valve assembly 52 is opened when the device 10 is rotated or spun about axis 16 to a speed in which a first centripetal force is reached. At or about the same speed and force, the plunger 50 of the plunger assembly 46 is actuated to introduce, for example, a suspension of cells into the first compartment 34 at a slow and steady rate. The speed at which the first valve assembly 52 opens can be from about 1000 rpm to about 3500, or from about 2500 rpm to about 3500 rpm. In one embodiment, the valve 52 opens at a speed of about 3000 rpm. In some embodiments, a baffle or dampener (not shown) is coupled to the second end 58 of the first valve assembly 52 to facilitate slow and gentle entry of the suspension of cells into the first compartment 34 such that the suspension of cells can be layered adjacent to a layer of wash solution, as described further below.

The device 10 further comprises a second valve assembly 60 having a tubular body 62 that extends from a first end 64 to a second end 66 and a second internal valve (not shown). In various embodiments, the device 10 comprises at least one of second valve assemblies 60. The second valve assembly 60 is positioned through the first inner wall 32, such that the first compartment 34 is in fluid communication with the second compartment 36 when the second valve is open. In some embodiments, the valve assembly 60 extends into the first compartment 34 and toward the central axis 16. As described further below, when the device is in use, the first end 64 of the valve assembly 60 is positioned at or near an interface between a suspension of cells and a wash solution. In this regard, the length of the body 62 is tuned based on the volume of cells loaded into the device 10. Therefore, device 10 can be made with various body 62 lengths. A user can select an appropriate device 10 based on the volume of cells to be washed. The second end 66 of the valve assembly 60 can either be in line with the inner wall 32 or it can extend radially into the second compartment 36. The second valve of the valve assembly 60 is normally in a closed position when the device 10 is not in use. During use, the second valve is actuated to an open position mechanically, electrically, or magnetically, at a predetermined centripetal force or pressure. Non-limiting examples of valves that are actuated by centripetal force and that are suitable for the second valve assembly 60 are described in U.S. Pat. No. 7,824,559 issued to Dorian et al. on Aug. 10, 20016, and U.S. Pat. No. 7,708,152 issued to Dorian et al. on May 4, 2010, both of which are incorporated herein by reference. In some embodiments the second valve of the second valve assembly 60 is opened when the device 10 is rotated or spun to a speed in which a second centripetal force is reached. The speed at which the second valve assembly 60 opens can be from about 2000 rpm to about 4000, or from about 2500 rpm to about 4000 rpm. In various embodiments, the valve 52 opens at a speed of about 3000 rpm or at a speed of about 3500 rpm. Typically, the second centripetal force is greater than the first critical centripetal force as described further below.

The device 10 is configured to be received by a base unit 90 that comprises a rotor. When engaged with the base unit 90, the base unit 90 is capable of spinning the device 10 about the axis 16 at various speeds to generate various centripetal forces.

With reference to FIG. 2, a device 10' is similar to the device 10 shown in FIGS. 1A-1B. However, in regard to the device 10', the first inner wall 32 is positioned at a distance D1 from the axis and the device 10' has a housing 12' that further defines a porous screen 68 that extends about and along the longitudinal axis 16 from the first surface 18 to the third surface 26 in the washing region 28. The porous screen 68 is positioned at a distance D2 from the axis 16, wherein D2 is shorter than D1. Therefore, the first inner wall 32 is concentric with the porous screen 68. In various embodiments, the position of the porous screen 68 is turned based on the volume of wash solution to be loaded into the device 10. For example, as the device 10' rotates about the axis 16, wash solution is forced against the first inner wall 32 to generate a surface that opposes the inner wall 32. The porous screen 68 is positioned at the surface of the wash solution opposing the first inner wall 32. Therefore various devices 10' can be made with the porous screen 68 located at various distances D2 from the axis 16. A user can select an appropriate device 10' based on the volume of wash solution to be used.

The porous screen 68 comprises pores that are sufficiently large to allow cells to pass through and sufficiently closely spaced such that cells will not jam or pile up significantly between the pores. In various embodiments, the porous screen 68 has pores with a mass cut off of from about 600 kDa to about 1000 kDa, or from about 700 kDa to about 800 kDa. In one embodiment, the screen 68 has pores with a mass cutoff of about 750 kDa. However, as described in more detail below, the pores should be sufficiently restrictive so that the screen 68 has a sufficient surface area to aid a suspension of cells to layer against a wash solution when the device 10' is in use. Therefore, the screen 68 can be a screen, frit, or open cell foam or mat. Accordingly, the screen 68 is positioned such that it will be immediately adjacent to, and in contact with, a surface of a wash solution when the device is rotating about the axis 16. In such embodiments, the second valve assembly 60 is positioned such that the first end 64 protrudes into the first compartment 34 at least to the screen 68.

With reference to FIGS. 3-8, the current technology provides a method for washing a suspension of cells with the device 10. As shown in FIG. 3, the method comprises loading or introducing a suspension of cells 70 into the barrel 48 of the plunger assembly 46 by way of the second inlet 44. The suspension of cells 70 comprises a suspension fluid 72 (which may include an enhancement composition) and a plurality of cells 74. As described above, the suspension of cells 70 can be a suspension of any cells that requires washing. In one embodiment, the suspension of cells comprises red blood cells and an enhancement composition. In another embodiment, the barrel 48 is pre-loaded with an enhancement composition and red blood cells are loaded into the barrel 48 via the second inlet 44 where the red blood cells are incubated and enhanced to generate the suspension of cells 70. The method also comprises loading or introducing a wash solution 76 into the first compartment 34 by way of the first inlet port 38. Any wash solution described herein can be used to wash the suspension of cells. However, in some embodiments the wash solution 76 has a density or specific gravity equal to or greater than the density or specific gravity of the suspension fluid 72. By having a wash solution 76 with higher density or specific gravity than the suspension fluid 72, a sharp and distinct interface forms between the wash solution 76 and the suspension of cells 70. After loading, the inlets 38, 44 are capped or plugged to prevent the respective solutions 76, 70 from leaking. Alternatively, in some embodiments the inlets 38, 44 are configured to prevent flow-back, such as with one-way inlet valves.

With reference to FIG. 4, the method comprises rotating the device 10 about the central axis 16 at a first speed to generate a first centripetal force by using the base unit 90. As the device 10 rotates, the first centripetal force causes the wash solution 76 to form a layer of wash solution 78 against the inner wall 32. Then, the device 10 is rotated at a second speed that is faster than the first speed until a second centripetal force is reached. As shown in FIGS. 5A and 5B, at a predefined centripetal force, the first internal valve of the first valve assembly 52 is opened, such as at a centripetal force in which the wash solution 76 has formed a layer 78 adjacent to the inner wall 32. At or near the same centripetal force, the plunger 50 of the plunger assembly 46 is actuated and depressed to slowly introduce the suspension of cells 70 into the first compartment 34. In various embodiments, the suspension of cells 70 is introduced into the first compartment 34 at or near the central axis 16. The centripetal force then causes the suspension of cells 70 to form a cell suspension layer 80 adjacent to the layer of wash solution 78, wherein the cell suspension layer 80 is closer to the central axis 16 than the layer of wash solution 78.

In embodiments including device 10' shown in FIG. 2, a volume of wash solution 76 is added such that it occupies a space between the inner wall 32 and the screen 68, such that the screen 68 is at a surface of the layer of wash solution 78 that opposes the first inner wall 32. The screen 68 encourages the suspension of cells 70 to form the cell suspension layer 80 against the layer of wash solution 78, such that the screen 68 is located at an interface between the layers 80, 78.

With reference to FIGS. 6A and 6B, the speed of rotation is increased to a third speed that is faster than the second speed to generate a third centripetal force. In various embodiments, the third speed is from about 2000 rpm to about 3400 rpm. In one embodiment, the third speed is about 3200 rpm. Here, the cells 74 in the cell suspension layer 80 pass through the layer of wash solution 78, thus separating the cells 74 from the suspension fluid 72 and wash solution 76 and forming a layer of clean cells 82 against the inner wall 32. As the cells 74 pass through the layer of wash solution 78, the cells 74 displace the layer of wash solution 78 and the wash solution 76 may blend with the suspension fluid 72. When the device 10' of FIG. 2 is used, the cells 74 pass through the pores of the screen 68 and then are forced to the inner wall 32.

As shown in FIG. 7, the method includes rotating the device 10 to a fourth speed that is faster than the third speed, until a fourth centripetal force is reached. At this centripetal force, or when all the cells 74 have passed through the layer of wash solution 78, the second interval valve in the second valve assembly 60 opens. Because the second valve assembly 60 extends into the first compartment 34 to, or about to, a surface 84 of the layer of cells 82, as described above, wash solution 76 and suspension fluid 72 flow through the second valve and into the second compartment 36, thus isolating the cells 74 from the wash solution 76 and suspension fluid 74. Loss of cells 74 can be minimized by ensuring that not too many cells are introduced into the device 10 such that the layer of cells 82 extends beyond the second valve assembly 60. When all of the wash solution 76 and suspension fluid 72 has entered the second compartment 36, rotation of the device 10 is stopped. As shown in FIG. 8, the wash solution 76 and suspension fluid 72 is isolated in the second compartment 36 and the clean cells 74 are isolated in the first center compartment 34. The method then comprises removing the clean cells 74 from the device 10 through the conduit 42 and outlet port 40. Optionally, the clean cells 74 can be stored or administered to a subject in need thereof with or without reconstitution. By performing the current method, a suspension of cells can be cleaned in from about 2 minutes to about 30 minutes, or in from about 10 minutes to about 15 minutes.

Another device 100 that can be used in the method for washing a suspension of cells is shown in FIG. 9A. FIG. 9B shows a cross-sectional view of the device 100 of FIG. 9A taken along line 9B. The device 100 comprises a housing 102 that defines a cylindrical outer wall 104 that extends about and along a central longitudinal axis 106 from a first inner surface 108 of a first end 110 to a second inner surface 112 of a second end 114. The first end 110 includes a first outer surface 111 and the second end 114 includes a second outer surface 115. In various embodiments, the first and second inner and outer surfaces 108, 112, 111, 115 are planar. The device 100 also includes a first cylindrical inner wall 116 and a second cylindrical inner wall 118 that extend about and along the axis 106 from the first inner surface 108 to the second inner surface 112. The first inner wall 116 defines a first central compartment 120. The second cylindrical wall 118 defines a second annular compartment 122 and a third annular compartment 124. The second compartment 122 is between the first compartment 120 and the third compartment 124. Additionally, the second and third compartments 122, 124 are concentric with, i.e., they share the same central axis 106, the first central compartment 120. Also, the device includes a relief compartment 126 that is adjacent to the second outer surface 115 and that extends about the central axis 106. The relief compartment 126 can have any cross-sectional geometry. However, in one embodiment, the relief compartment 126 has a three-dimensional shape of a cone and has a cross-sectional geometry of a triangle, such that it defines a collection point or sump 128. The relief compartment 126 is in fluid communication with the second compartment 122 by means of at least one aperture, or an annular opening 130.

The device 100 also comprises a first inlet port 132 and a second inlet port 134 positioned at the first end 110. The first and second inlet ports 132, 134 are in fluid communication with the first compartment 120 and the second compartment 122, respectively. Also, the device 100 includes an outlet port 136. The outlet port 136 is in fluid communication with the relief compartment 126 by way of a conduit 138 that traverses the first compartment 120. In one embodiment, the conduit 138 extends to or near the collection point or sump 128 of the relief compartment. Due to the aperture or opening 130, the outlet port 136 can optionally be used as an inlet port, equivalent to the second inlet port 134, for introducing a substance to the second compartment 122. Although the first and second inlet ports 132, 134 and the outlet port 136 are shown protruding from the device 100, it is understood that all the ports 132, 134, 136 can be in line, i.e., flat, with the first surface 108 to preclude protrusions when the device 100 is in use.

The device 100 also comprises a first valve assembly 140 comprising a tubular body 142 that extends from a first end 144 to a second end 146 and a first internal valve (not shown) positioned through the first inner wall 116, such that the first compartment 120 is in fluid communication with the second compartment 122 when the first valve is open. The valve of the first valve assembly 140 is closed prior to use of the device. During use, the first valve is actuated to an open position mechanically, electrically, or magnetically, at a predetermined centripetal force or pressure. Non-limiting examples of valves that are actuated by centripetal force and that are suitable for the first valve assembly 140 are described in U.S. Pat. No. 7,824,559 issued to Dorian et al. on Aug. 10, 20016, and U.S. Pat. No. 7,708,152 issued to Dorian et al. on May 4, 2010, both of which are incorporated herein by reference. In some embodiments the first valve of the first valve assembly 140 is opened when the device 100 is rotated or spun to a speed in which a first centripetal force is reached. The speed at which the first valve assembly 140 opens can be from about 1000 rpm to about 3500, or from about 2500 rpm to about 3500 rpm. In one embodiment, the valve assembly 140 opens at a speed of about 3000 rpm. In one embodiment, the tubular body 142 of the first valve assembly 140 extends into the second compartment 122 to facilitate layering of cells against a layer of wash solution. In various embodiments, a baffle or dampener (not shown) is coupled to the second end 146 of the first valve assembly to facilitate gentle and efficient layering of a suspension of cells against a layer of a wash solution. The first valve assembly 140 is positioned anywhere along the first inner wall 116. However, in some embodiments, the first valve assembly 140 is positioned through the first inner wall 116 at or near the second surface 112.

The device 100 also comprises a second valve assembly 148 comprising a tubular body 150 that extends from a first end 152 to a second end 154 and a second internal valve (not shown) positioned through the second inner wall 118, such that the second compartment 122 is in fluid communication with the third compartment 124 when the second valve is open. The valve of the second valve assembly 148 is normally closed prior to use of the device. During use, the second valve is actuated to an open position mechanically, electrically, or magnetically, at a predetermined centripetal force or pressure. Non-limiting examples of valves that are actuated by centripetal force and that are suitable for the second valve assembly 148 are described in U.S. Pat. No. 7,824,559 issued to Dorian et al. on Aug. 10, 20016, and U.S. Pat. No. 7,708,152 issued to Dorian et al. on May 4, 2010, both of which are incorporated herein by reference. In some embodiments the second valve of the second valve assembly 148 is opened when the device 100 is rotated or spun to a speed in which a second centripetal force is reached. The speed at which the second valve assembly 148 opens can be from about 2000 rpm to about 4000, or from about 2500 rpm to about 4000 rpm. In various embodiments, the valve of the second valve assembly 148 opens at a speed of about 3000 rpm or at a speed of about 3500 rpm. In one embodiment, the tubular body 150 of the second valve assembly 148 extends into the second compartment 122 such that the second end 154 is positioned at or near an interface between a layer of cells and a layer of wash solution when the device 100 is in use. In this regard, the length of the body 150 is tuned based on the volume of cells loaded into the device 100. Therefore, devices 100 can be made with various body 150 lengths. A user can select an appropriate device 100 based on the volume of cells to be washed. The second valve assembly 148 is positioned anywhere along the second inner wall 118. However, in some embodiments, the second valve assembly 148 is positioned through the second inner wall 118 at or near the first surface 108. In various embodiments, the device 100 comprises at least one second valve assembly 148.

In some embodiments, the device 100 further includes an optional porous screen 156 that extends about and along the longitudinal axis 106 from the first inner surface 108 to the second inner surface 112. The optional porous screen 126 is positioned between the first and second inner walls 116, 118. Accordingly, the porous screen 156 is concentric with the first and second inner walls 116, 118. In various embodiments, the position of the porous screen 156 is turned based on the volume of wash solution to be loaded into the device 100. For example, as this device 100 rotates about the axis 16, wash solution is forced against the first inner wall 116 to generate a surface that opposes the inner wall 116. The porous screen 156 is positioned at the surface of the wash solution opposing the first inner wall 116. Therefore various devices 100 can be made with the porous screen 156 located at various distances D2 from the axis 106. A user can select an appropriate device 100 based on the volume of wash solution to be used. The porous screen 156 comprises pores that allow cells and fluid to pass through and sufficiently closely spaced such that cells will not jam or pile up significantly between the pores. In various embodiments, the porous screen 156 has pores with a mass cutoff of from about 600 kDa to about 1000 kDa, or from about 700 kDa to about 800 kDa. In one embodiment, the screen 156 has pores with a mass cutoff of about 750 kDa. However, as described in more detail below, the pores should be sufficiently restrictive so that the screen 156 has a sufficient surface area to aid a suspension of cells to layer against a wash solution when the device 100 is in use. Therefore, the screen 156 can be a screen, frit, or open cell foam or mat. Accordingly, the screen 156 is positioned such that it will be immediately adjacent to, and/or contact with, a surface of a wash solution when the device 100 is rotating about the axis 106. In such embodiments, the second valve assembly 148 is positioned such that the second end 154 protrudes into the second compartment 122 at least to the screen 156.

The device 100 is configured to be received by a base unit 190 that comprises a rotor (not shown). When engaged with the base unit 190, the base unit 190 is capable of spinning the device 100 about the axis 106 at various speeds to generate various centripetal forces.

With reference to FIGS. 10-16, the current technology provides a method for washing a suspension of cells with the device 100. As shown in FIG. 10, the method comprises loading or introducing a wash solution 160 into the second compartment 122 of the device 100 by way of the second inlet port 134. In various embodiments, the wash solution 160 is selected from the group consisting of water, saline, dextrose, saline with 5% dextrose, dextran 40 (such as, for example, 10% dextran 40 in 0.9% sodium chloride or in 5% dextrose), hetastarch solutions (such as, for example, 6% hetastarch in 0.9% sodium chloride), and phosphate buffered saline. The wash solution 160 flows through the opening or aperture 130 and into the relief compartment 126. Nonetheless, as shown in FIG. 10, the volume of the wash solution 160 is sufficient to fill the relief compartment 126 and a portion of the second compartment 122. In an alternative embodiment, the wash solution 160 is introduced to the device 100 by way of the outlet 136 and its corresponding conduit 138.

As shown in FIG. 11, the method also includes loading or introducing a suspension of cells 162 into the first compartment 120 of the device 100 by way of the first inlet port 132. The suspension of cells 162 includes a suspension fluid 164 and a plurality of cells 166. In various embodiments, the plurality of cells 166 is selected from the group consisting of red blood cells, white blood cells, platelets, and combinations thereof. The suspension of cells 162 may also include cell fragments and cellular debris. The suspension fluid 164 comprises a fluid for suspending the plurality of cells 166 and, in some embodiments, an enhancement composition. In some embodiments, an enhancement composition is preloaded into the device 100 through inlet 134 and a solution of cells is then added into the device through the first inlet 132 to generate the suspension of cells 162. The suspension of cells 162 is then incubated for a predetermined period of time. Because the first valve in the first valve assembly 140 is closed, the suspension of cells will not flow into the second compartment 122 and mix with the wash solution 160. It is understood that the wash solution 160 and suspension of cells 162 can be loaded in any order.

With reference to FIG. 12, the method comprises rotating or spinning the device 100 about the axis 106. Rotating or spinning can be performed in clockwise or counter-clockwise directions. As the device 100 is spinning, centripetal force pushes the suspension of cells 162 against the first inner wall 116. Likewise, the centripetal force pushes the wash solution 160 against the second inner wall 118 to generate a layer of wash solution 168. When the screen 156 is present, the pores receive a portion of the layer of the wash solution 168. For example, the device 100 can be spun at a speed of from about 500 to about 1600 rpm in order to push the suspension of cells 162 against the first inner wall 116. In one embodiment, the suspension of cells 162 are pushed against the first inner wall 116 when the device 100 reaches a speed of about 1000 rpm.

Figure 13:
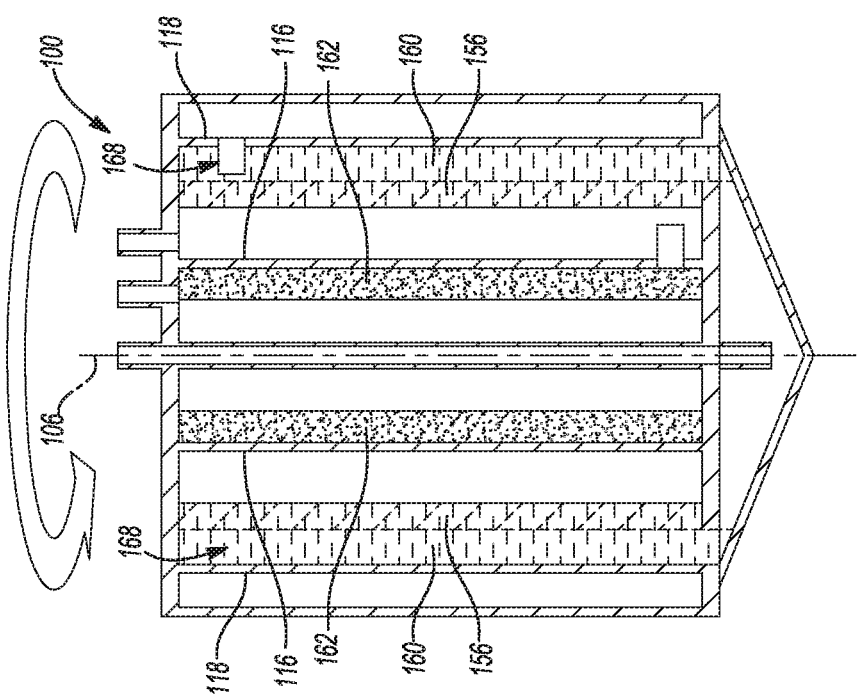

As shown in FIG. 13, the method includes opening the first valve of the first valve assembly 140 when a first centripetal force is reached, such as the centripetal force in which the suspension of cells 162 is pressed against the first inner wall 116 and the layer of wash solution 168 has formed at the at the second inner wall 118. The suspension of cells 162 flows through the first valve assembly 140 and into the second chamber 122. When the porous screen 156 is included in the device 100, it has a sufficient surface area to facilitate layering of the suspension of cells 162 against the layer of wash solution 168 to generate a layer of suspended cells 170. Nonetheless, the layer of suspended cells 170 also forms when the screen 156 is not included. In various embodiments, not shown a baffle or dampener is coupled to the first valve assembly 140 to facilitate slow and gentle flow of the suspension of cells into the second compartment 122.

As shown in FIG. 14, as the speed of rotation increases, centripetal force forces the plurality of cells 166 through the layer of wash solution 168 and against the second inner wall 118. As the plurality of cells 166 passes through the layer of wash solution 168, unwanted components, such as cell fragments, cellular debris, or and suspension fluid 164 stays behind and may blend into the layer of wash solution 168. Thus a layer of clean cells 172 forms against the second inner wall 118. Simultaneously, the layer of clean cells 172 displaces the layer of wash solution 168 so that an interface 174 is formed between the layer of clean cells 172 and the layer of wash solution 168. The interface 174 is positioned such that the second end 154 of the second valve assembly 148 is at or near the interface 174.

Figure 16:
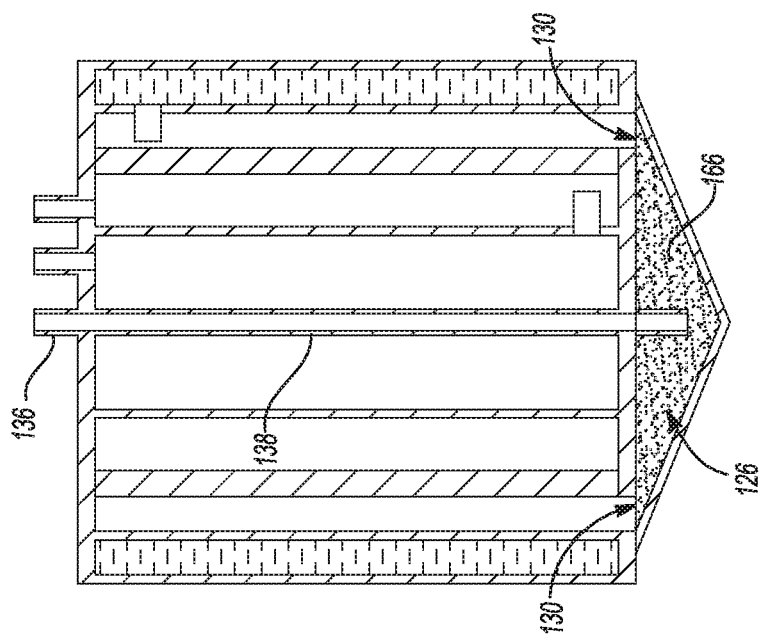

With reference to FIG. 15, when the device 100 is rotated or spun at a speed that generates a second centripetal force or the centripetal force in which the layer of clean cells 172 has been completely formed, the method includes opening the second internal valve of the second valve assembly 148. Because the second valve assembly 148 extends into the second compartment 122 to, or near, a surface 174 of the layer of cells 172, as described above, the centripetal force then forces the wash solution 160 and the suspension fluid 164 through the second valve assembly and into the third compartment 124, thus isolating the layer of clean cells 172. As shown in FIG. 16, when the device stops rotating, gravity pulls the clean cells 166 through the opening or apertures 130 and into the relief compartment 126. The clean cells are then removed from the device 100 through the conduit 138 and outlet 136. By performing the current method, a suspension of cells can be cleaned in from about 2 minutes to about 30 minutes or in from about 10 minutes to about 15 minutes.

Figure 17:
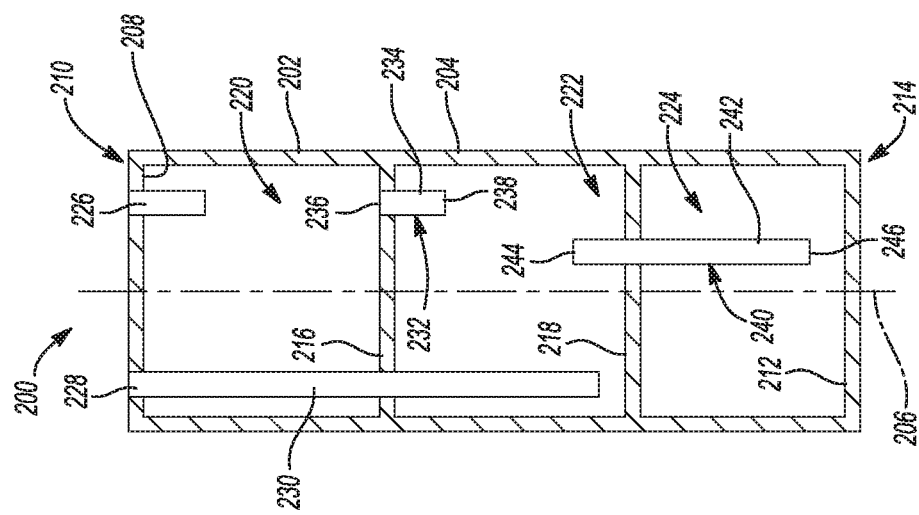
FIG. 17 is a cross-sectional perspective of a third device according to the present technology.

The present technology provides another device 200 for washing a suspension of cells, as shown in FIG. 17. The device comprises a housing 202 that defines a cylindrical wall 204 that extends about and along a central longitudinal axis 206 from a first inner surface 208 of a first end 210 to a second inner surface 212 of a second end 214. The device 200 includes a first planar separator 216 positioned orthogonal to the axis 206 and to the wall 204 and a second planar separator 218 positioned orthogonal to the axis 206 and to the wall 204. The first and second separators 216, 218 define a first compartment 220, a second compartment 222, and a third compartment 224 consecutively from the first end to the second end. Additionally, the device 200 comprises a first inlet 226 positioned at the first end 210 that is in fluid communication with the first compartment 220 and a bi-functional port 228 positioned at the first end 210 that is in fluid communication with the second compartment 222 through a conduit 230. The conduit 230 extends to or near the first separator 216. In an alternative embodiment (not shown), the bi-functional port 228 is a second inlet and the device further comprises an outlet port that is in fluid communication with the second compartment 222 by way of a second conduit.

The device 200 also include a first valve assembly 232 that includes a tubular body 234 that extends from a first end 236 to a second end 238, and a first internal valve (not shown). Non-limiting examples of valves that are actuated by centripetal force and that are suitable for the first valve assembly 232 are described in U.S. Pat. No. 7,824,559 issued to Dorian et al. on Aug. 10, 20016, and U.S. Pat. No. 7,708,152 issued to Dorian et al. on May 4, 2010, both of which are incorporated herein by reference. The first valve assembly 232 is positioned in the first separator 216 such that the first and second compartments 220, 222 are in fluid communication when the first valve is open. Additionally, the device 200 includes a second valve assembly 240 that includes a tubular body 242 that extends from a first end 244 to a second end 246, and a second internal valve (not shown). Non-limiting examples of valves that are actuated by centripetal force and that are suitable for the second valve assembly 240 are described in U.S. Pat. No. 7,824,559 issued to Dorian et al. on Aug. 10, 20016, and U.S. Pat. No. 7,708,152 issued to Dorian et al. on May 4, 2010, both of which are incorporated herein by reference. The second valve assembly 240 is positioned in the second separator 218 such that the second and third compartments, 222, 224 are in fluid communication when the second valve is open. In various embodiments, the length of the body 242 is tuned based on the volume of cells to be loaded into the device 200. After rotating the device 200, the first end 244 of the body 242 is positioned, at or near an interface between cells and a wash solution. Devices 200 can be made with various tube body 242 lengths. A user can select an appropriate device 200 based on the volume of cells to be washed. The first and second valves of the first and second valve assemblies can be actuated mechanically, electrically, or magnetically, at a predetermined centripetal force or pressure. In one embodiment, the first valve of the first valve assembly 232 is configured to open at a first centripetal force and the second valve of the second valve assembly 240 is configured to open at a second centripetal force. Typically, the second centripetal force is greater than the first centripetal force. For example, the first valve can be opened when the device 200 reaches a speed of from about 1000 rpm to about 3500 rpm. And the second valve can be opened when the device 200 reaches a speed of from about 2000 rpm to about 4000 rpm. The device 200 is configured to be rotated by a centrifuge rotor.

Figure 18:
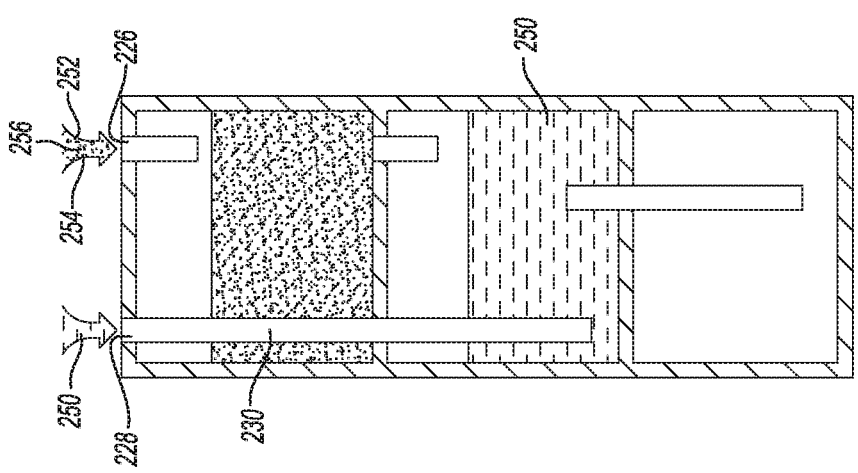

A method for using the device 200 for washing a suspension of cells is also provided. With reference to FIG. 18, the method comprises introducing a wash solution 250 into the second compartment 222 of the device 200 through the bi-functional port 228 and its corresponding conduit 230. Here, the bi-functional port 228 is used as a second inlet. In various embodiments, the wash solution 250 is selected from the group consisting of water, saline, dextrose, saline with 5% dextrose, dextran 40 (such as, for example, 10% dextran 40 in 0.9% sodium chloride or in 5% dextrose), hetastarch solutions (such as, for example, 6% hetastarch in 0.9% sodium chloride), and phosphate buffered saline. The method also includes introducing a suspension of cells 252 into the first compartment 220 through the first inlet 226.

The suspension of cells 252 comprises a suspension fluid 254 and a plurality of cells 256. The suspension of cells 252 can also comprise cell fragments, cellular debris, or a combination thereof. The plurality of cells 256 can include, for example, red blood cells, white blood cells, platelets, or combinations thereof. In various embodiments, the density or specific gravity of the wash solution 250 is equal to or greater than the density or specific gravity of the suspension fluid 254. By having a wash solution 250 with higher density or specific gravity than the suspension fluid 254, a sharp and distinct interface forms between the wash solution 250 and the suspension of cells 252. It is understood that introducing the wash solution 250 and suspension of cells 252 can be performed in any order. In one embodiment, the first compartment 220 is preloaded with an enhancement composition and cells 256 are introduced into the enhancement composition through the first inlet 226 to generate the suspension of cells 252 within the device 200. The suspension of cells is incubated for a predetermined period of time and the method is thereafter resumed.

Figure 19:
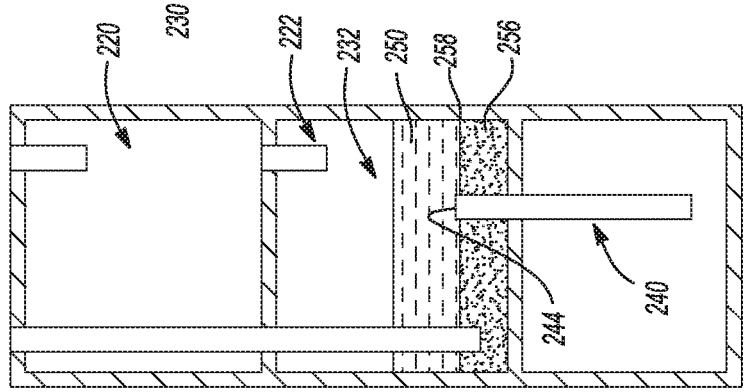

After loading the device 200, the device 200 is placed into a centrifuge rotor that is placed within a centrifuge. The centrifuge rotor is balanced by a blank device, a second loaded device 200, or a centrifuge tube of the same weight. The centrifuge is turned on and the rotor begins to spin. With reference to FIG. 19, when a first centripetal force is reached, the first valve of the first valve assembly is opened. The suspension of cells 252 is pulled through the first valve and into the wash solution 250. Because they are denser than the wash solution 250, the cells 256 are pulled through the wash solution 250 and settle on the second separator 218, thus displacing the wash solution 250 and separating the cells 256 from the suspension fluid 254 and wash solution 250. The suspension fluid 254 may blend with the wash solution 250 depending on their relative densities and an interface 258 is formed between the cells 256 and the wash solution 250 blended with suspension fluid 254. Accordingly, the cells 256 that settle on the second separator 218 are clean. As shown in FIG. 19, the first end 244 of the second valve assembly 240 extends into the second compartment 222 to or near the interface 258.

Figure 20:
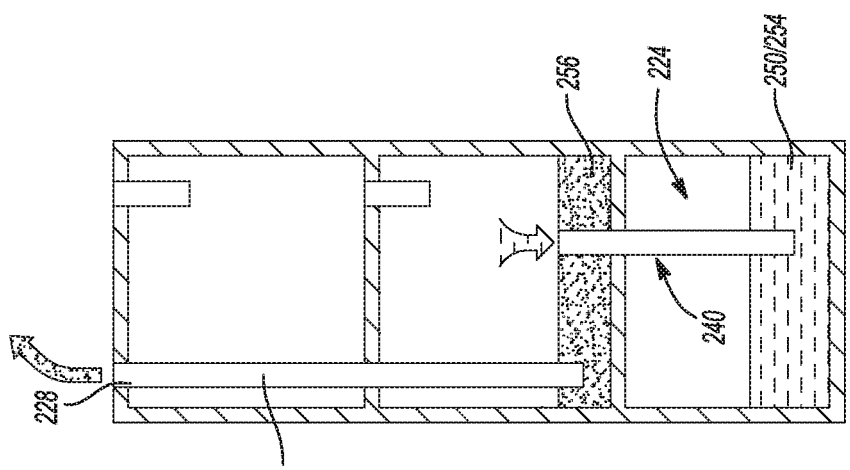
FIGS. 18-20 are graphic illustrations of various stages of the device of FIG. 17 when being used to wash a suspension of cells.

As shown in FIG. 20, when a second centripetal force is reached, or at the centripetal force in which all the cells 256 have passed through the wash solution 250, the second valve of the second valve assembly 240 is opened. The wash solution 250, suspension fluid 254, and other unwanted components, such as cell fragments and cellular debris, are pulled through the second valve assembly 240 and into the third compartment 224, thus isolating the clean cells 256. When the centrifuge is stopped, the method includes removing the clean cells 256 through the conduit 230 and the bi-functional port 228, which is now used as an outlet. By performing the current method, a suspension of cells can be cleaned in from about 2 minutes to about 30 minutes or in form about 10 minutes to about 15 minutes.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for washing a suspension of cells, the device comprising:
   a housing defining a cylindrical outer wall that extends about and along a central longitudinal axis from a first inner surface of a first end to a second inner surface of a second end,
   a first cylindrical inner wall that extends about and along the longitudinal axis from the first inner surface to the second inner surface, the first inner wall defining a first compartment and a second compartment adjacent to and concentric with the first compartment;
   a first valve assembly including a first valve, the first valve assembly positioned through the first inner wall such that the first compartment is in fluid communication with second compartment when the first valve is open at a first centripetal force;
   a plunger assembly comprising a plunger valve, the plunger assembly in fluid communication with the first compartment when the plunger valve is open at plunger valve centripetal force, the plunger valve centripetal force being different from the first centripetal force;
   a first inlet port; and
   an outlet port.

2. The device according to claim 1, further comprising a second inner wall that extends about and along the longitudinal axis from the first inner surface to the second inner surface, the second inner wall positioned between the first inner wall and the cylindrical outer wall to define a third compartment adjacent to and concentric with the second compartment.

3. The device according to claim 2, further comprising a porous screen that extends about and along the longitudinal axis from the first inner surface to the second inner surface and positioned between the first inner wall and the second inner wall, wherein the porous screen comprises pores configured to permit cells to pass through.

4. The device according to claim 2, further comprising a second valve assembly including a second valve, the second valve assembly positioned through the second inner wall such that the second compartment is in fluid communication with the third compartment when the second valve is open.

5. The device according to claim 4, wherein the first valve is configured to open at the first centripetal force and the second valve is configured to open at a second centripetal force that is greater than the first centripetal force.

6. The device according to claim 4, wherein the second valve assembly extends from a first end to a second end of a valve body, and wherein the first end extends into the second compartment to a point where a cell: solution interface will form during use.

7. The device according to claim 1, further comprising a relief compartment positioned adjacent to a second outer surface disposed opposite to the second inner surface, the relief compartment being in fluid communication with the second compartment.

8. The device according to claim 7, wherein the outlet port is positioned on the first end, the outlet port being in fluid communication with the relief compartment through a conduit.

9. The device according to claim 1, wherein the first inlet port is in fluid communication with the first compartment and the outlet port is configured to be used as a second inlet port.

10. The device according to claim 1, wherein the first inlet port is in fluid communication with the first compartment, and the device further comprises a second inlet port in fluid communication with the second compartment.

11. The device according to claim 1, wherein the first inlet port and the outlet port are in fluid communication with the first compartment, and wherein the outlet port is in fluid communication with the first compartment through a conduit that extends adjacent to the second inner surface.

12. The device according to claim 1, wherein the first inner wall is positioned at a distance D1 from the longitudinal axis and the device further comprises a porous screen that extends about and along the longitudinal axis from the first inner surface to the second inner surface and is positioned at a distance D2 from the longitudinal axis, wherein D2 is less than D1, and wherein the porous screen comprises pores configured to permit cells to pass through.

13. The device according to claim 1, the plunger assembly further comprising a barrel and a plunger, the plunger assembly positioned outside of the first and second compartments.

14. The device according to claim 1, wherein the first centripetal force is less than the plunger valve centripetal force.

15. The device according to claim 14, the plunger assembly further comprising a plunger configured to be actuated at the plunger valve centripetal force.

16. The device according to claim 1, wherein the first valve assembly extends from a first end to a second end of a valve body, and wherein the first end extends into the first compartment to a point where a cell: solution interface will form during use.

17. A device for washing a suspension of cells, the device comprising:
- a cylindrical outer wall that extends about and along a central longitudinal axis between a first end and a second end,
- a cylindrical inner wall that extends about and along the central longitudinal axis between the first end and the second end, the first inner wall defining a first compartment and a second compartment concentric with the first compartment, the inner wall positioned a distance D1 from the central longitudinal axis;
- a first valve assembly having a first valve configured to open at a first centripetal force, the first compartment in fluid communication with second compartment when the first valve is open;
- a porous screen configured to allow cells to pass through, the porous screen positioned a distance D2 from the central longitudinal axis, wherein D2 is less than D1;
- a first port; and
- a second port.

18. The device of claim 17, wherein the first valve comprises a body having a first end and a second end, the first end extending into the first compartment a distance determined by a volume to be loaded into the device.

19. The device of claim 18, further comprising a plunger assembly including a second valve configured to open at a second centripetal force that is different from the first centripetal force, the plunger assembly in fluid communication with the first compartment when the plunger valve is open.

20. The device of claim 17, wherein the plunger assembly comprises a plunger configured to be actuated at the second centripetal force.

* * * * *